(12) United States Patent
Onoue et al.

(10) Patent No.: US 9,517,204 B2
(45) Date of Patent: Dec. 13, 2016

(54) PHARMACEUTICAL COMPOSITION FOR INHALATION

(75) Inventors: Satomi Onoue, Shizuoka (JP); Shizuo Yamada, Shizuoka (JP)

(73) Assignees: SHIONOGI & CO., LTD., Osaka (JP); SHIZUOKA PREFECTURAL UNIVERSITIES CORPORATION, Shizuoka (JP)

( * ) Notice: Subject to any disclaimer, the term of this patent is extended or adjusted under 35 U.S.C. 154(b) by 0 days.

(21) Appl. No.: 14/344,467

(22) PCT Filed: Sep. 13, 2012

(86) PCT No.: PCT/JP2012/073514
§ 371 (c)(1),
(2), (4) Date: Mar. 27, 2014

(87) PCT Pub. No.: WO2013/039167
PCT Pub. Date: Mar. 21, 2013

(65) Prior Publication Data
US 2014/0341998 A1    Nov. 20, 2014

(30) Foreign Application Priority Data
Sep. 14, 2011   (JP) .................. 2011-200150

(51) Int. Cl.
| | | |
|---|---|---|
| A61K 9/14 | (2006.01) | |
| A61K 47/26 | (2006.01) | |
| A61K 31/4418 | (2006.01) | |
| A61K 9/00 | (2006.01) | |
| A61M 15/00 | (2006.01) | |
| A61M 11/00 | (2006.01) | |

(52) U.S. Cl.
CPC .............. *A61K 9/14* (2013.01); *A61K 9/0075* (2013.01); *A61K 9/145* (2013.01); *A61K 9/146* (2013.01); *A61K 31/4418* (2013.01); *A61K 47/26* (2013.01); *A61M 11/002* (2014.02); *A61M 15/00* (2013.01); *A61M 2202/064* (2013.01)

(58) Field of Classification Search
CPC .... A61K 47/26; A61K 31/4418; A61K 9/146; A61K 9/0075; A61K 9/14; A61K 9/145; A61M 15/00; A61M 2202/064
See application file for complete search history.

(56) References Cited

U.S. PATENT DOCUMENTS

| 7,550,133 | B2 * | 6/2009 | Hale et al. ............... 424/45 |
|---|---|---|---|
| 2004/0109827 | A1 | 6/2004 | Onoue et al. |
| 2007/0117783 | A1 | 5/2007 | Brueck-Scheffler et al. |
| 2009/0258075 | A1 | 10/2009 | Hale et al. |
| 2010/0040691 | A1 | 2/2010 | Richards et al. |
| 2010/0087416 | A1 | 4/2010 | Griffith et al. |
| 2012/0192861 | A1 | 8/2012 | Surber |
| 2013/0310424 | A1 | 11/2013 | Surber |

FOREIGN PATENT DOCUMENTS

| CN | 1486175 A | 3/2004 |
|---|---|---|
| EP | 1 036 562 | 9/2000 |
| JP | 2002-284703 | 10/2002 |
| JP | 2003-034652 | 2/2003 |
| JP | 2010-132605 | 6/2010 |
| JP | 2011-93849 | 5/2011 |
| WO | 90/09176 | 8/1990 |
| WO | 94/26249 | 11/1994 |
| WO | 2007/064738 | 6/2007 |
| WO | 2010/048716 | 5/2010 |
| WO | 2012/106382 | 8/2012 |

OTHER PUBLICATIONS

Masayoshi et al. JP 2010/132605; published: Jun. 17, 2010; English Machine Translation obtained on Apr. 6, 2015.*
Extended European Search Report issued Mar. 25, 2015 in corresponding European Patent Application No. 12832375.5.
International Search Report dated Oct. 9, 2012 issued in International (PCT) Application No. PCT/JP2012/073514.
S. Onoue et al., "Novel Methodology for Predicting Photogenotoxic Risk of Pharmaceutical Substances Based on Reactive Oxygen Species (ROS) and DNA-Binding Assay", Journal of Pharmaceutical Sciences, vol. 98, No. 10, Oct. 2009, pp. 3647-3658.
S. Onoue et al., "Inhalable Powder Formulation of Pirfenidone with Reduced Phototoxic Risk for Treatment of Pulmonary Fibrosis", Phar. Res. vol. 30, pp. 1586-1596, 2013.
Y. Seto et al., "Photosafety Assessments on Pirfenidone: Photochemical, Photobiological, and Pharmacokinetic Characterization", Journal of Photochemistry and Photobiology B: Biology, vol. 120, pp. 44-51, 2013.
Y. Kawabata et al., "Stable Dry Powder Inhaler Formulation of Tranilast Attenuated Antigen-Evoked Airway Inflammation in Rats", European Journal of Pharmaceutics and Biopharmaceutics, vol. 77, No. 1, pp. 178-181, 2011.
S. Onoue et al., "Development of Inhalable Nanocrystalline Solid Dispersion of Tranilast for Airway Inflammatory Disease", Journal of Pharmaceutical Sciences, vol. 100, No. 2, pp. 622-633, Feb. 2011.
S. Onoue et al., "In Vitro and In Vivo Characterization on Amorphous Solid Dispersion of Cyclosporine A for Inhalation Therapy", Journal of Controlled Release, vol. 138, No. 1, pp. 16-23, 2009.
International Preliminary Report on Patentability (Chapter I or Chapter II) and Translation of the Written Opinion of the International Searching Authority mailed Mar. 27, 2014 in International application No. PCT/JP2012/073514.
"Dispersible Dry Powder Formulations for Targeted Lung Delivery of Pirfenidone for Treatment of Idiopathic Pulmonary Fibrosis", (Abstract), AAPS Annual Meeting and Exposition, Nov. 12, 2009.

* cited by examiner

*Primary Examiner* — Ali Soroush
*Assistant Examiner* — Genevieve S Alley
(74) *Attorney, Agent, or Firm* — Wenderoth, Lind & Ponack, L.L.P.

(57) ABSTRACT

The present invention relates to a powder formulation which reduces side effect risk of a medicine having a side effect of drug-induced photodermatosis and increases therapeutic effect, and relates to the method for producing the same. Said powder formulation makes inhalation therapy possible by carrying out aerosolization easily, and since pharmacological effect in lung local part is increased, it is possible to decrease the dose. Skin transmigration of said medicine is controlled by a lung specific delivery technology, and photodermatosis which is a side effect can be controlled.

15 Claims, 8 Drawing Sheets

PHARMACEUTICAL COMPOSITION FOR INHALATION

The present application is a national stage application filed under 35 U.S.C. 371 of international application no. PCT/JP2012/073514, filed Sep. 13, 2012, and it claims priority under 35 U.S.C. 119 to Japan Patent Application No. 2011-200150, filed Sep. 14, 2011.

TECHNICAL FIELD

Present invention relates to a pharmaceutical composition which can control the whole body exposure of a medicine, especially transmigration to skin of a medicine having a side effect of drug-induced photodermatosis. The present invention also relates to a respirable powder formulation which is easy to be handled pharmaceutically and makes it possible to retain the uniform drug content because of improvement in dispersibility.

BACKGROUND ART

Inhalation therapy has been applied for treatment of lung and respiratory tract disease, diagnosis of disease, transrespiratory tract and transpulmonary whole body medication, prophylaxis of disease, transrespiratory tract immunity desensitization therapy, etc. as a medicinal use of transrespiratory. However, the adaptation-determining method of this therapy is fully examined at neither of the cases. Therefore, development of the corresponding respirable formulation is desired.

As features of a general respirable formulation, recognized are 1) quick expression of drug effects, 2) gradual reduction of side effects, 3) possibility of small dose administration, 4) avoidance of the first-pass effect, etc. When a target region is lung, the respirable formulation is equipped with further outstanding features by having a large surface area equal to small intestine. In applying the respirable formulation as a targeting therapy, it is necessary to consider a selection-criteria method of the respirable formulation from viewpoint of not only efficacy to disease but a generation method of medicine particles, arrival parts, and relevancy of the basic physical properties of medicine to them. Now, the respirable formulation is used for bronchodilator, mucosa solubilizer, antibiotic, antiallergic agent, steroid, vaccine, physiological saline, etc., and in the case of their clinical application, site of action of inhalant, mechanism of the action, composition, direction for use, etc. are considered to be of important factors.

Recent years, in treatment of bronchial asthma or chronic lung disease, a Dry Powder Inhaler (Dry Powder Inhaler, DPI) has come to attract attention. This form has advantage that, in addition of the feature as above-mentioned respirable formulation, medicine can be stored with stable form for a long period of time. In DPI, there is a close relationship between a particle diameter of medicine particles being respired by patient and a deposition to respiratory tract [Pharmacia (1997) Vol. 33, No. 6, and 98-102], and the aerodynamics correlation is accepted in what kind of medicine particle diameter deposits inside trachea and lung. Specifically, it is generally known that the optimal sizes of medicine particles which can reach bronchus or lung are particles which have an aerodynamics diameter of about 1 to 6 μm [Int. J. Pharm. (1994) 101 and 1-13].

Preferably, particles of several μm or less reach alveolus, and since they are efficiently absorbed from lung mucosa and migrate into blood, the particle size becomes important.

However, the more the particles get fine, the more the fluidity of powder gets worse and, as a result, decline of filling precision and handling property at the time of production gets worried. Then, in order to solve these problems in handling of the DPI formulation, the method mentioned below is well known which mixes micronized particles with coarse particles, such as lactose and erythritol, being used as carrier. According to this method, by making micronized particles adhere to the carrier surface via intermolecular interaction, cohesive force of micronized particles become weaker, and the particle diameter becomes large further as a whole, and thus, the fluidity of the formulation is improved. The other methods including granulation of a medicine and a surface treatment method are mentioned (Patent Document 1).

Here, pirfenidone (henceforth PFD) is the world's first anti-fibrosis agent for approval acquisition to be applied for idiopathic pulmonary fibrosis. The action mechanism is production modulation for various cytokines, such as inflammatory cytokine and anti-inflammation cytokine, and for growth factors which participate in fibrosis formation, and the anti-fibrosis effect is shown based on complex effects, such as fibroblast multiplication depressant action and collagen production depressant action. In comparison between this agent and prednisolone, while prednisolone showed only anti-inflammatory activity, this agent showed both anti-inflammatory activity and anti-fibrosis effect, then, consequently, it is expected that more effective therapeutic results than steroid can be brought about. Although it has been sold since 2008 in Japan, and is widely used for pulmonary fibrosis, many of patients who have taken this agent have showed a side effect of drug-induced photodermatosis, and their expression frequency results in about 60 percent. In order to avoid this problem, suitable dosage form which can easily show effect on lung local part has been desired. However, only oral formulation has been marketed till the present, and more preferable dosage form design aiming at stability and local administration has not been examined irrespective of the high demand. That is, development is desired strongly for new dosage forms which will reduce photodermatosis risk, a side effect of pirfenidone, and will bring about safer pulmonary fibrosis treatment. As DPI formulations in which micronized particles were made to adhere to the carrier surface, a formulation using lactose as a carrier (Patent Document 2), a cyclosporin formulation (Non-patent Document 1), a tranilast formulation (Patent Document 3, Non-patent Documents 2-3), etc. have been reported. However, in any references, the transmigration control to the skin and the photodermatosis risk fall of medicine by the above-mentioned DPI formulation are not described.

LIST OF PRIOR ARTS

[Patent Document 1] WO99/27911

[Patent Document 2] Japanese Patent 4125512

[Patent Document 3] Japanese Patent Publication 2011-93849 A

[Non-patent Document 1] Journal of Controlled Release (2009), 38(1), 16-23

[Non-patent Document 2] Journal of Pharmaceutical Sciences (2011), 100(2), 622-633

[Non-patent Document 3] European Journal of Pharmaceutics and Biopharmaceutics (2011) 77(1) 178-181

SUMMARY OF INVENTION

Problems to be Solved by the Invention

Medicines migrate to the whole body generally via blood by oral administration, then accordingly, they migrate also to the skin to some extent, and this is thought to causes a side effect. Accordingly, a subject of the invention is to provide a formulation which can control the whole body exposure of a medicine having a side effect of drug-induced photodermatosis, especially transmigration of the medicine to the skin. Still more preferably is a provision of a respirable formulation wherein the medicine, especially pirfenidone, shows a sufficient efficacy and outstanding inhalation characteristics.

Means for Solving the Problems

Inventors of the present invention repeated researches extensively to solve the above-mentioned problems, and as a result, they came to complete the present invention. That is, pirfenidone, which is a medicine having a side effect of drug-induced photodermatosis, was ground by a grinder such as a jet mill in the coexistence of excipients to afford micronized particles having a diameter which can reach lung aerodynamically, and subsequently, the micronized particles obtained were mixed well with carriers which have a good conformity with the obtained-micronized particles and have a diameter which can reach systems respiratorium aerodynamically, then a formulation with very high content-uniformity was successfully obtained to complete the present invention. When an experimental lung inflammation model rat was medicated with this formulation in respiratory tract, while a control group showed very high lung disorder property and neutrophilic-leukocyte inflammation, a group administered with pirfenidone in a respirable formulation was able to be controlled powerfully against these conditions. When pirfenidone of dose (30 mg/kg) which does not show anti-inflammatory activity was administered orally to rat, photodermatosis was not caused, but transmigration to the skin was observed promptly. On the other hand, when pharmacologically effective dose, for example, of 0.1 mg/kg or more of the respirable powder formulation of pirfenidone was administered to the subject in respiratory tract, as compared with oral administration, significant suppression of the skin extraction rate was observed. From these data, it can be said that the respirable powder formulation of the present invention decreases dose remarkably by delivering a medicine directly to the pharmacodynamic target tissue, and moreover, in connection with it, the formulation shows such a prominent effect that a drug-induced photodermatosis risk which is a critical side effect may be reduced. That is, the present invention provides the followings (1)-(22).

(1) A powder formulation comprising micronized particles with a mean particle diameter of 20 μm or less comprising a drug having a side effect of drug-induced photodermatosis and an excipient, and a carrier having a mean particle diameter of 10~200 μm.

(2) The powder formulation according to (1) above, wherein the drug having a side effect of drug-induced photodermatosis is 1 or 2 or more selected from the group consisting of antibiotics, anticancer drug, antiepileptic drug, antidepressant, antifungal, antihistamine, antimalarial, gout drug, psychotropic drug, cardiovascular remedy, diuretic, antilipemic, non-steroid anti-inflammatory agent, phototherapy agent, letinoid, and pulmonary fibrosis treating agent.

(3) The powder formulation according to (1) above, wherein the drug having a side effect of drug-induced photodermatosis is a pulmonary fibrosis treating agent.

(4) The powder formulation according to (1) above, wherein the drug having a side effect of drug-induced photodermatosis is pirfenidone.

(5) The powder formulation according to any one of (1)-(4) above, wherein the micronized particles and the carriers form complexes.

(6) The powder formulation according to (5) above, wherein a particle diameter of the micronized particles is smaller than a mean particle diameter of the carriers.

(7) The powder formulation according to any one of (1)-(6) above, wherein the excipient and/or the carrier are saccharides.

(8) The powder formulation according to (7) above, wherein saccharides are lactose.

(9) The powder formulation according to any one of (1)-(6) above, wherein the excipient and/or the carrier are sugar alcohols.

(10) The powder formulation according to (9) above, wherein the sugar alcohols are erythritol.

(11) The powder formulation according to any one of (1)-(6) above, wherein the excipient is macromolecular polymers.

(12) The powder formulation according to any one of (1)-(6) above, wherein the excipient is erythritol and the carrier is lactose.

(13) The powder formulation according to any one of (1)-(12) above, wherein a ratio between the drug having side effects of drug-induced photodermatosis and the excipient is in the range of 1:5000~10:1 in weight ratio.

(14) The powder formulation according to any one of (1)-(13) above, wherein the ratio between the micronized particles and the carriers is in the range of 1:100~10:1 in weight ratio.

(15) The powder formulation according to any one of (1)-(14) above, wherein a mean diameter of the micronized particles is in the range of 1~9 μm.

(16) The powder formulation according to any one of (1)-(15) above, wherein the powder formulation is a transpulmonary respirable formulation.

(17) The powder formulation according to (4) above, wherein the drug-induced photodermatosis of pirfenidone has been reduced as compared with an oral administration formulation.

(18) A process for producing the formulation according to any one of (1)-(17) above, wherein the micronized particles with a mean particle diameter of 20 μm or less comprising a drug having a side effect of drug-induced photodermatosis and an excipient are mixed with a carrier having a particle diameter of 10~200 μm.

(19) The process according to (18) above, wherein the micronized particles are prepared by mixing the drug having a side effect of drug-induced photodermatosis and the excipient, and micronizing the mixture by a jet mill.

(20) The process according to (19) above, wherein the micronized particles and the carriers are mixed in a container made from nylon or polyethylene.

(21) The process according to any one of (18)-(20) above, wherein the micronized particles and the carriers form complexes.

(22) A respirable formulation obtained by the process according to any one of (18)-(21) above.

Effects of the Invention

According to the pharmaceutical composition of the present invention, it is possible to aerosolize easily a medicine powder, such as pirfenidone, which has a side effect of drug-induced photodermatosis, and by delivering the medicine very specifically to lung, treatment of inflammatory lung disease, pulmonary fibrosis, etc. is remarkably enabled by low dose compared with an oral administration, and simultaneously, by preventing a skin transmigration of the medicine, it is possible to reduce the photodermatosis risk which is a main side effect of the medicine. And, the pharmaceutical composition of the present invention can be produced more preferably as a uniform-content formulation.

BRIEF DESCRIPTION OF DRAWINGS

In FIG. 3(A), the symbols represent; □/■: pirfenidone, ▽/▼: 8-methoxy psoralen (MOP), and △/▲: sulisobenzone (□▽△ are singlet oxygen and ■▼▲ are superoxide). In FIG. 3(B), symbols represent: □: pirfenidone solution, ◇: pirfenidone powder, and ●: respirable powder formulation of pirfenidone.

EMBODIMENTS TO CARRY OUT THE INVENTION

Figure 1:
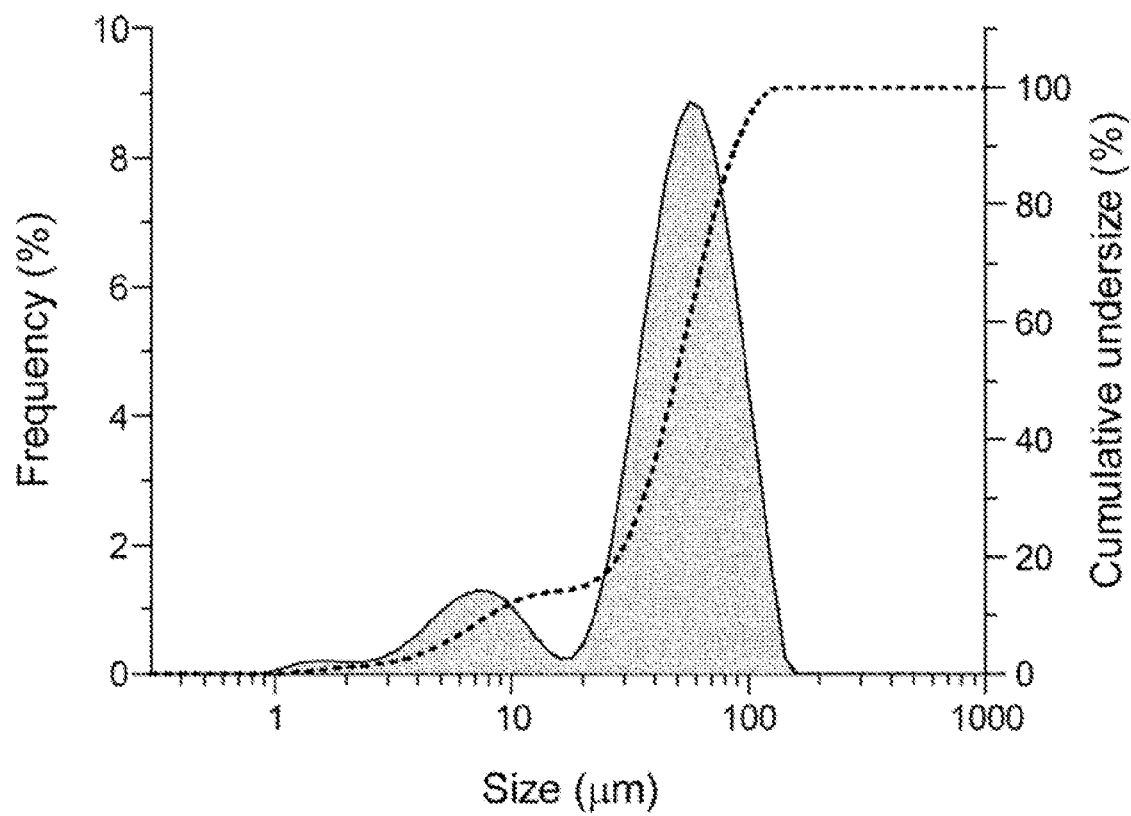
FIG. 1 shows a particle size distribution at the time when the formulation 1 was aerosolized.

Hereinafter, the present invention is explained in detail.

[1] Medicine having a side effect of drug-induced photodermatosis Especially as medicines having a side effect of drug-induced photodermatosis, although not limited specifically, the medicines described in Table 2 of Current Drug Safety, (2009), vol 4, pp 123-126 are mentioned. For example, they are antibiotic, anticancer agent, antiepileptic drug, antidepressant, antifungal, antihistamine, antimalaric, gout drug, psychotropic drug, cardiovascular treating agent, diuretic, antilipemic, non-steroid anti-inflammatory agent, phototherapy agent, letinoid, pulmonary fibrosis treating agent, etc. Ciprofloxacin, enoxacin, lemefloxacin, sulfanilamide, sulfamethoxazole, tetracycline, etc. are mentioned as antibiotic. Fluorouracil, methotrexate, etc. are mentioned as the anticancer agent. Carbamazepine, phenobarbital, etc. are mentioned as the antiepileptic drug. Amitriptyline, amoxapine, etc. are mentioned as the antidepressant. Flucytosine, itraconazole, etc. are mentioned as the antifungal. Bromapheniramine, diphenhydramine, etc. are mentioned as the antihistamine. Chloroquine, kinin, etc. are mentioned as the antimalaric. Benzbromarone etc. are mentioned as the gout suppressant. Chlorpromazine, haloperidol, etc. are mentioned as the psychotropic drug. Captopril, clofibrate, etc. are mentioned as the cardiovascular treating agent. Furosemide, acetazolamide, etc. are mentioned as the diuretic. Glibenclamide, tolbutamide, etc. are mentioned as the antilipemic. Indomethacin, ibuprofen, etc. are mentioned as the non-steroid anti-inflammatory agent. 8-MOP (xanthotoxin), foscan, photofrin, etc. are mentioned as the phototherapy agent. Acitretin, etretinate, isotretinoin, etc. are mentioned as the letinoid. Pirfenidone is mentioned, for example, as a treatment agent for pulmonary fibrosis. In the present invention, pirfenidone is especially preferable. As pirfenidone being used in the present invention, the method of preparing the same is not limited in particular, and what is used or will be used in the future as drugs is included, such as crystal, amorphous, salt, hydrate, and solvate thereof.

[2] Excipient

The excipient used herein is the one which is generally used for the purpose of gain in weight, dilution, filling, supporting of form, etc. of solid preparations, such as powders and a tablet. The excipient is effective in order to improve the solubility of a medicine, and/or to reduce the self-condensation ability of a medicine. Accordingly, although a water-soluble excipient is preferred, the excipient which absorbs moisture remarkably is not preferred for the property of this formulation. The excipient which is biologically inactive and is expected to be metabolized to some extent may be used. Water-soluble polymers can also be used, and there is no limitation for them as far as they are allowable as a medicine. Specific examples of such excipients that may be used include sugars such as lactose, glucose, saccharose, trehalose, sucrose; sugar alcohols such as erythritol, mannitol, sorbitol; starches; macromolecular polymers such as crystalline cellulose, methyl cellulose, hydroxypropyl cellulose, hydroxypropyl methylcellulose, carmellose sodium, pullulan, dextrin, gum arabic, agar, gelatin, tragacanth, sodium alginate, polyvinylpyrrolidone, polyvinyl alcohols; stearic acid; fatty acids and salts thereof; waxes; calcium sulfate; calcium carbonate; talc; titanium oxide; and light anhydrous silicic acid. A combination of one or more sorts selected from these may be used. Preferable excipients in the present invention are one or more selected from the group consisting of sugars, sugar-alcohols, macromolecular polymers and calcium carbonates, and lactose or saccharose is preferable as sugars, erythritol, sorbitol, or mannitol is preferable as sugar-alcohols, and carmellose calcium, pullulan, polyvinylpyrrolidone, or methylcellulose is preferable as macromolecular polymers. Especially preferable excipient is lactose or erythritol.

[3] Carrier

In the present invention, a carrier is used for preventing the medicine to condense before the administration of the powder formulation, and for improving absorption efficiency as the transpulmonary respirable formulation at the time of administration, by forming a complex between the medicine and the excipient (mentioned afterward). Especially, when an inhalation operation using an inhaler is carried out for the purpose of application in bronchus or lung, the inhaler is used for efficiently separating the excipient from the medicine after inhalation and, as a result, for improving absorption efficiency of the medicine. When the carrier is used for DPI formulation design, it is desirable to release the medicine definitely from the capsule or device, and to separate the medicine from the carrier surface with high probability. It is necessary to perform the formulation design in considering enough these points. In the case of using carriers, fluidity of the formulation, prevention of the medicine aggregation, and the propriety of dose increase and decrease, etc. become important. From these viewpoints, carriers in the present invention are preferably powdered. As selection criteria of carriers, easiness and workability for handling are required, not to mention toxicity or physicochemical stability. In order to clear these problems, lactose, the stability of which is also established conventionally, and is neutral, has little reactivity, and also has sweet taste a little, is useful in many points, and its usefulness is confirmed as the carrier for DPI [Int. J. Pharm. (1998) 172, 179-188]. As carriers which can be used in the present invention, sugars such as glucose, fructose, saccharose, maltose and dextran besides lactose, sugar-alcohols such as erythritol, sorbitol, and mannitol, common excipients such as calcium sulfate, calcium carbonate, talc, and titanium oxide can be mentioned also, and there is no limitation in particular. Preferable carrier is sugars or sugar-alcohols, and more preferable carrier is lactose or erythritol and, lactose is especially preferable.

When the pharmaceutical composition of the present invention is a form being administered to the patient using an inhaler, the carrier is the one which has a particle diameter permitted aerodynamically. Specifically, a range of the mean particle diameter of the carrier is 10~200 μm. When you want to make the carrier act only as a carrier from the point of dosage form design, it is known that enlarging of the particle diameter is enough for it. However, simultaneously, if the particle diameter is enlarged, it is also a well-known fact that the carrier retains at throat or the oral cavity. Accordingly, when it is more desirable to prevent the carrier itself from reaching even lung in spite of its biological inactivity, it is satisfactory if the mean particle diameter shall be at least 10 μm or more. When further best conditions are required, material selection after considering the conformity etc. of a main agent and a mixed excipient is desired. However, unless big problems are observed in particular, it is preferable to select a carrier of the same quality of material as that of the excipient.

[4] Mixing and grinding process of the medicine having a side effect of drug-induced photodermatosis and the excipient Manufacture of the powder formulation for inhalation administration of the present invention contains a mixing and grinding process of the medicine having a side effect of drug-induced photodermatosis and the excipient. Trituration is performed, for example, at the same time as the excipient and the medicine having a side effect of drug-induced photodermatosis are mixed using an aerodynamic grinder. The method is not limited for producing the powder formulation of the present invention, but a suitable method which a person skilled in the art usually uses can be used. It can be suitably determined by the kinds of medicine and excipient, the size of final particles, etc. whether which method is used or not. A crystallized state of the compound and the formulation characteristics, such as adhesion and dispersing ability, are correlated in many cases, and, consequently the latter processing method should be selected desirably in this step. However, in the case where pirfenidone is used as the medicine expressing a side effect of drug-induced photodermatosis, and erythritol is used as the excipient, because of the very high crystal orientation of pirfenidone, a good trituration mixture can be obtained even if any step is selected.

Particles which comprise the obtained medicine and excipient according to the above-mentioned step are called micronized particles in this specification.

In the present invention, although a general drying-grinding process can be used for trituration of the medicine and the excipient, it is preferred to use especially an aerodynamic grinder. Specifically, devices which grind small quantity efficiently in a laboratory, such as a mortar and a ball mill, are used frequently as a common drying-grinding machine. As a ball mill, a rolling ball mill, a centrifugal ball mill, a vibration ball mill, and a planetary ball mill are known, and these can perform trituration by principles, such as grinding, rotation, vibration, and impact. There are many devices, as industrial use, aiming at efficiently grinding a lot of materials, such as a medium churning type mill a high velocity revolution trituration and impact mill, and a jet mill. There are a disc mill and a roller mill as a high velocity revolution trituration mill, and as a high velocity revolution impact mill, there are devices such as a cutter mill (knife mill), a hammer mill (atomizer), a pin mill, a screen mill, etc., which perform trituration also according to rotation impact in addition to shearing. As a jet mill, many mainly perform trituration with impact. As for the kind, there are the most orthodox particle-particle collision type, a particle-collision plate collision type, and a nozzle sucking type (blow off). In particular, it is preferred that the trituration is performed by the jet mill.

As for a weight ratio of the medicine having a side effect of drug-induced photodermatosis and the excipient in the formulation of the present invention, a range of 1:5000~10:1 is preferable. If the medicine increases more than this range, trouble may result in the content uniformity, and if the excipient increases more than this range, for a certain kind of medicine, there is a danger of elimination of the pharmacological activity. The weight ratio of the medicine having a side effect of drug-induced photodermatosis and the excipient is more preferably 1:100~5:1, and still more preferably, 1:10~2:1, and most preferably, 3:2.

By grinding process, the medicine having a side effect of drug-induced photodermatosis is mixed with the excipient by homogeneity, and it is ground so that the mean particle diameter may become micronized particles of 20 μm or less. The diameter within these ranges makes it possible for the micronized particles to reach the part of objects, such as bronchus and lung. Mean particle diameter of micronized particles is 10 μm or less, preferably, 1~9 μm, more preferably, and 3μ8 μm, most preferably.

[5] Mixing step of carriers and micronized particles Subsequently, the micronized particles obtained in the above-mentioned mixing/trituration step are mixed with carriers, and till the time of administration, and let stable complexes to be formed. In the specification of the present application, the complex represents a molecular aggregate formed by condensation of a medicine with an excipient and a carrier via self-condensation capability caused by a molecular interaction of the medicines. Mixing of carriers and micronized particles can be performed by using a well-known mixer generally. There are mainly a batch system and a continuous system in the mixer, and further in the batch system, there are two sorts of a rotated type and a fixed mount type. There are a horizontal drum mixer, a V shaped rotary mixer, a double cone type mixer, and a cubic type mixer in the rotated type, and there are a screw type (perpendicularity, level) mixer, a revolution screw type mixer, and a ribbon type (perpendicularity, level) mixer in the fixed mount type. The continuous system is also divided into two sorts, a rotated type and a fixed mount type. As for the rotated type, a horizontal drum mixer and a level cone type mixer are known, and a screw type (perpendicularity, level) mixer, a ribbon type (perpendicularity, level) mixer, and a rotation disk type mixer are known for the fixed mount type. In addition, the mixing method using aerodynamic grinders, such as a medium churning type mill, a high velocity revolution grinding and an impact mill, and a jet mill, is possible. It is possible to make a uniform mixed-preparation by using and agitating a container which consists of product made of nylon, polyethylene, or the material having property similar to them.

It is preferred to make the weight ratio of micronized particles and carriers into the range of 1:100~10:1. If the micronized particles increase more than this range, trouble may result in the content uniformity, and if the carriers increase more than this range, for a certain kind of medicine, elimination of the pharmacological activity is worried about. Weight ratios of micronized particles and carriers are more preferably 1:50~1:1, still more preferably 1:20~1:5 and most preferably 1:10.

A ratio of mean particle diameters of micronized particles and carriers is preferably in the range of 1:1~1:50, and more preferably 1:5~1:20.

[6] Inhaler

When the complex obtained in the above-mentioned step is administered to a patient as the powder formulation for inhalation administration, the subject can be medicated by per-mucosal administration such as transpulmonary administration, nasal administration, etc. When the route of administration is transpulmonary administration, specifically, the powder formulation can be prescribed for the patient by using any inhalers generally used in the art.

As the inhaler, devices for inhalation transpulmonary, such as Spin haler, E-haler, Flow-Caps, Jet haler, Disk haler, Rotor haler, Inspirer ease, Inhalation eight, etc. and quantitative atomizers, etc., can be used but it is not limited to these.

Example 1

(1) Preparation of Micronized Particles Used for Respirable Powder Formulation

After mixing a pirfenidone crystal (about 60 mg) with various excipients (about 40 mg), micronization was performed with a jet mill, and thus, micronized particles were prepared. As the excipient, erythritol (Nikken formation), lactose (DMV), carmellose calcium (Daicel Chemical Industries), pullulan (Hayashibara), polyvinyl pyrrolidone (BASF), methyl cellulose (Shin-Etsu Chemical), sorbitol (Kao), calcium carbonate (Kanto Kagaku) or white soft sugar (Mitsui Sugar) was used.
(Grinding Conditions)
Used instrument: A-O-Jet Mill (Seishin Enterprise)
Feeding method: Auto feeder
Supply air pressure: 6.0 kg/cm$^2$G
Grinding air pressure: 6.5 kg/cm$^2$G
Dust collecting method: Outlet bug (polyethylene)
The yield was as follows, respectively.

| | |
|---|---|
| Micronized particles 1 (excipient: erythritol) | 75.8% |
| Micronized particles 2 (excipient: lactose) | 61.0% |

-continued

| | |
|---|---|
| Micronized particles 3 (excipient: carmellose sodium) | 59.9% |
| Micronized particles 4 (excipient: pullulan) | 74.6% |
| Micronized particles 5 (excipient: polyvinyl pyrrolidone) | 68.5% |
| Micronized particles 6 (excipient: methyl cellulose) | 71.3% |
| Micronized particles 7 (excipient: sorbitol) | 88.3% |
| Micronized particles 8 (excipient: mannitol) | 68.4% |
| Micronized particles 9 (excipient: calcium carbonate) | 72.9% |
| Micronized particles 10 (excipient: white soft sugar) | 60.8% |

(2) Preparation of Respirable Powder Formulation

The micronized particles obtained in (1) were put into a STAT-3S antistatic bag made from polyethylene (20×30 cm, Asanuma industrial Corporation Ltd.) with carriers, and sealed after being filled with air, and the content was mixed by shaking by hand for about 3 minutes, then the formulations 1-20 shown in. Table 1 were obtained. Samples were taken from five places arbitrarily after mixing, the amount of the drug contained was measured by UPLC/ESI-MS, and the uniformity of the content was thus confirmed. At this time, erythritol (Nikken formation, mean particle diameter: 20~30 μm) or lactose (DMV, mean particle diameter: 50~60 μm) was used as carriers. The weight ratio of the micronized particles and the carriers was 1:10.

Example 2

Particle-Size-Distribution Measurement of Respirable Powder Formulation

Figure 2:
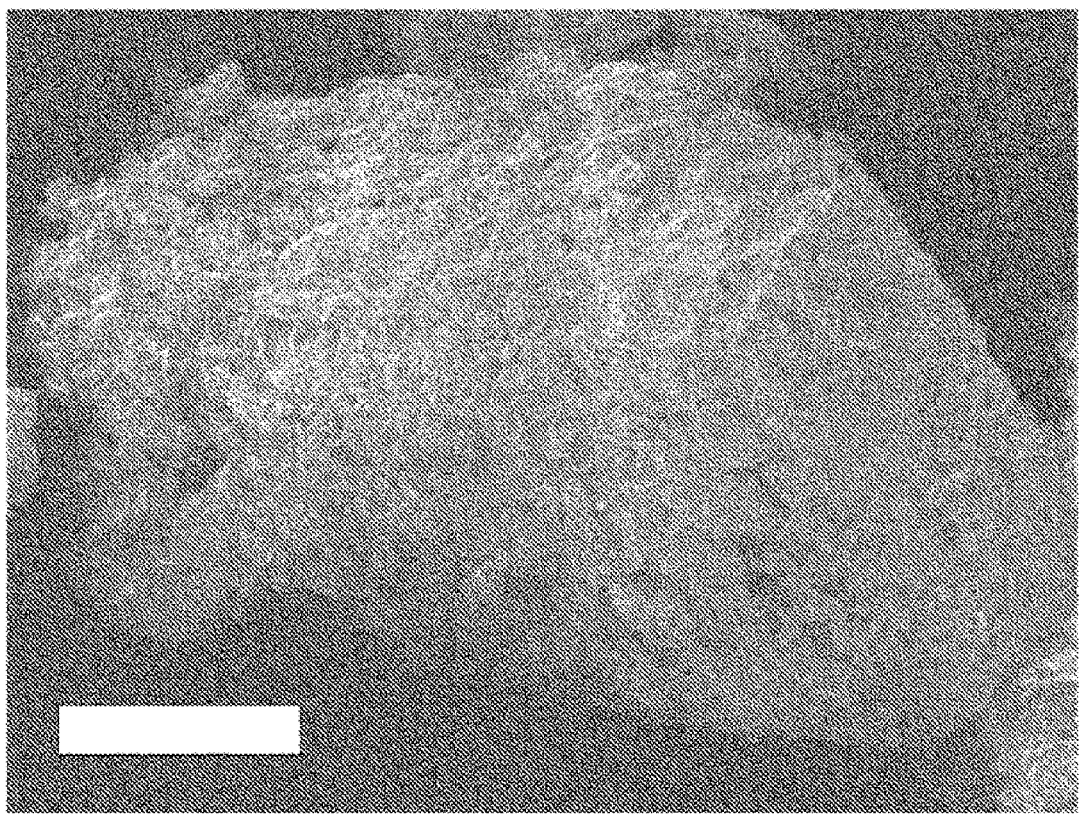
FIG. 2 shows a SEM image at the time when carriers and micronized particles (excipient and pirfenidone particles) formed complexes.

As a result of evaluating the mixture of micronized particles and carriers using a dry type laser diffraction device (LMS-300, Seishin Enterprise), aerosolization of any formulation was easily carried out under pressure of 0.2 MPa. FIG. 1 shows a particle size distribution of the mixture (formulation 1) of the micronized particles 1 and lactose carriers. Two main peaks are mainly shown, and the peak with a mean particle diameter of 7 μm originates in the micronized particles, and the peak with a mean particle diameter of 60 μm originates in the carriers. As for other formulations, the ranges of a mean particle diameter of the micronized particles were 3.0~8.0 μm. It is considered that the carriers remain in respiratory tract at the time of inhalation, and the micronized particles may reach bronchus or lung at the time of inhalation. The mean particle diameters of the micronized particles in the formulations 1~20 obtained by analysis are shown in Table 1. The SEM image which photographed the situation where the micronized particles (excipient and pirfenidone grains) were actually complexed with carriers (lactose) is shown (FIG. 2). It can be observed that the pirfenidone grains, which were micronized by jet milling and turned into single spherical grains, adhered to lactose without any significant agglomeration.

TABLE 1

| | Excipient | Carrier | Mean paraticle diameter of Micronized particles (μm) |
|---|---|---|---|
| Formulation 1 | erythritol | lactose | 7.0 |
| Formulation 2 | lactose | lactose | 5.6 |
| Formulation 3 | carmellose sodium | lactose | 7.1 |
| Formulation 4 | pullulan | lactose | 6.4 |

TABLE 1-continued

|  | Excipient | Carrier | Mean paraticle diameter of Micronized particles (μm) |
|---|---|---|---|
| Formulation 5 | polyvinylpyrrolidone | lactose | 6.5 |
| Formulation 6 | methyl cellulose | lactose | 7.3 |
| Formulation 7 | sorbitol | lactose | 3.7 |
| Formulation 8 | mannitol | lactose | 6.2 |
| Formulation 9 | calcium carbonate | lactose | 7.8 |
| Formulation 10 | saccharose | lactose | 4.6 |
| Formulation 11 | erythritol | erythritol | 5.3 |
| Formulation 12 | lactose | erythritol | 7.6 |
| Formulation 13 | carmellose sodium | erythritol | 3.8 |
| Formulation 14 | pullulan | erythritol | 5.6 |
| Formulation 15 | polyvinylpyrrolidone | erythritol | 4.1 |
| Formulation 16 | methyl cellulose | erythritol | 3.3 |
| Formulation 17 | sorbitol | erythritol | 7.4 |
| Formulation 18 | mannitol | erythritol | 4.8 |
| Formulation 19 | calcium carbonate | erythritol | 6.2 |
| Formulation 20 | saccharose | erythritol | 3.6 |

Example 3

Photoreactivity Testing and Photostability Testing

Figure 3:
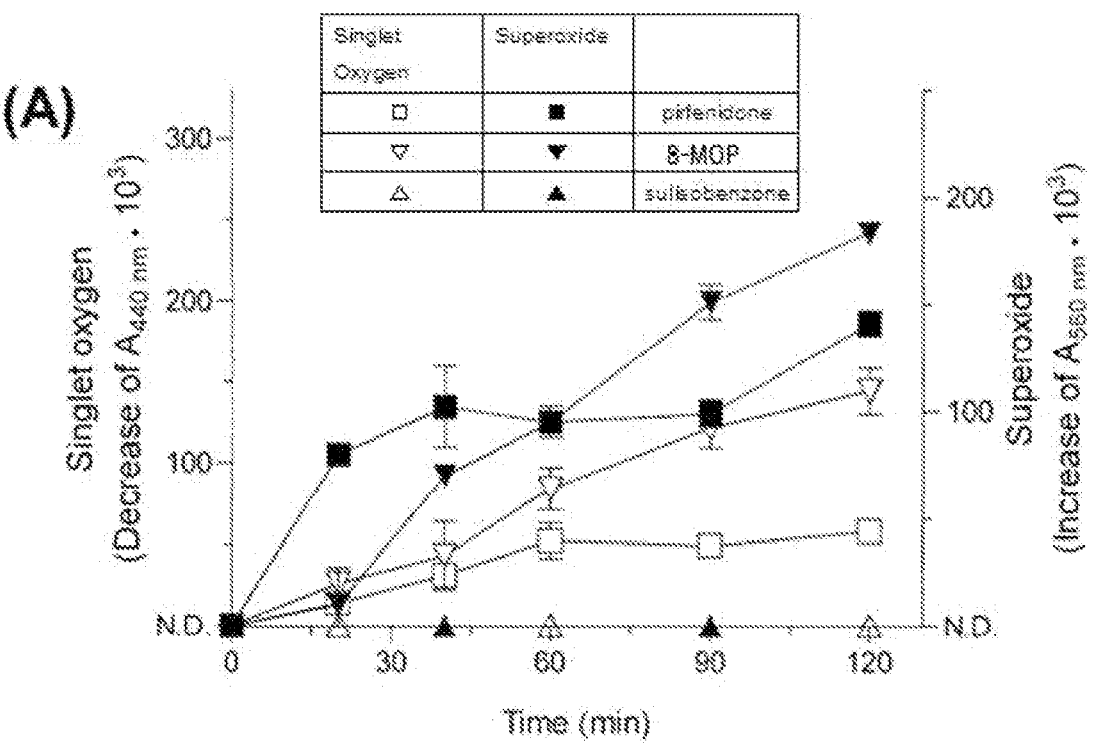
FIG. 3 shows the result of photoreactivity test of each compound.
Figure 3:
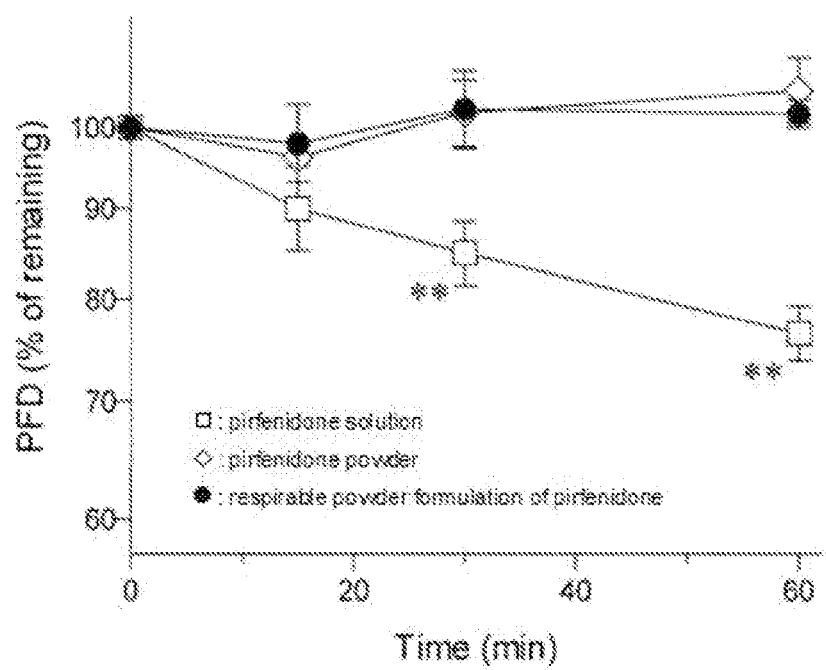

FIG. 3 (A) shows the result of a reactive oxygen species (ROS) assay which was carried out to measure the photoreactivity of pirfenidone. This assay was established to monitor the generation of ROS, such as singlet oxygen and superoxide, from photoirradiated chemicals, and ROS generation would be indicative of the photochemical reactivity of tested chemicals.

Sulisobenzone, a potent UV absorber, has no ability to generate ROS when exposed to simulated sunlight (250 $W/m^2$); therefore, sulisobenzone can be identified to be less photoreactive. In contrast, 8-methoxypsoralen (MOP) is known as a phototoxic and photoreactive chemical. Although 8-MOP slightly exceeded pirfenidone in ROS generation, both chemicals were identified to be photoreactive, as shown in FIG. 3 (A). When such photoreactivity and photoirritability are taken into consideration, pirfenidone can be said to raise concerns about photostability.

Here, in respirable formulation of pirfenidone, both liquid and dry powder formulations can be considered in theory. Then, to clarify the photochemical properties in more detail, photostability testing was carried out. First, none of the pirfenidone samples tested showed any degradation in chromatographic analysis when they were stored at 25° C. for 1 h under light protection. Exposure of PFD solution to simulated sunlight (250 $W/m^2$) resulted in the degradation of pirfenidone, and it was likely to follow first-order kinetics with an apparent first-order degradation rate of 0.31±0.03 $h^{-1}$ as shown in FIG. 3 (B). In contrast, no significant degradation was observed in pirfenidone powder under the same irradiation conditions. In general, photosensitive chemicals in a solution state are far more prone to photodegradation than solid samples due to the high permeability of light and increased mobility of photochemically excited molecules and reactive species. From this, taken together with the result shown in FIG. 3 (B), dry powder formulation, rather than liquid formulation, is preferable as a respirable formulation of pirfenidone.

Example 4

Assessment of the Respirable Powder Formulation (Formulation 1) by Cascade Impactor In order to conduct investigation on the aerodynamic particle size of fine powders, an examination was carried out using a cascade impactor which is an artificial respiratory tract and a lung model. A body of the impactor is composed of piles in eight stages and a final filter, combined with a velocity indicator and a suction pump. The fundamental method, which is a procedure described in "Multistage Cascade Impactor Apparatus" of USP 2000 "Physical Tests and Determinations/Aerosols" was applied. The specified method is as follows.

Figure 4:
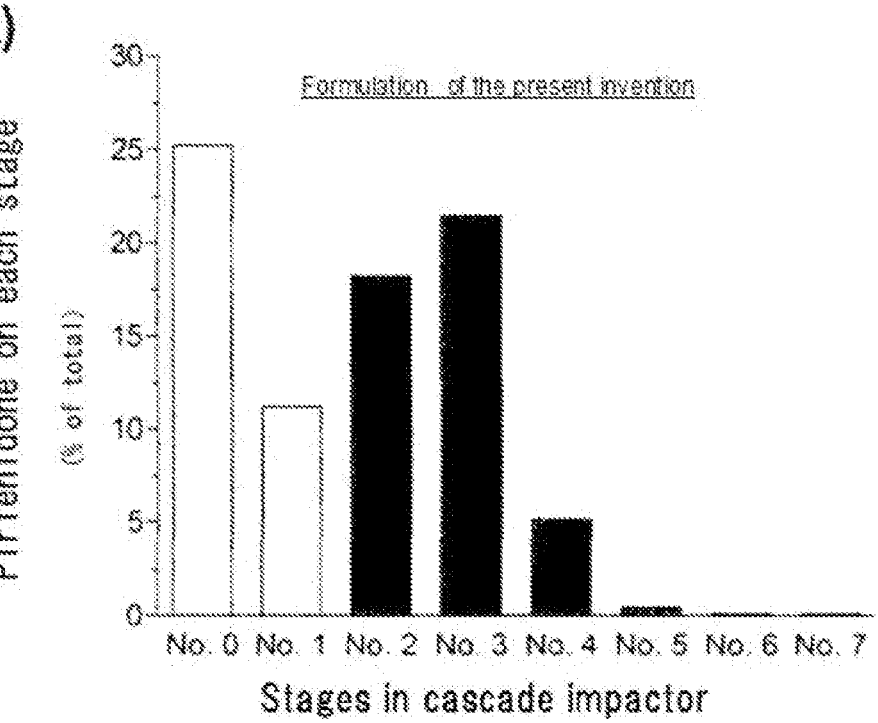
FIG. 4 shows the amount of pirfenidone in each stage in the body of cascade impactor in the case of use or non-use of the carrier.
Figure 4:
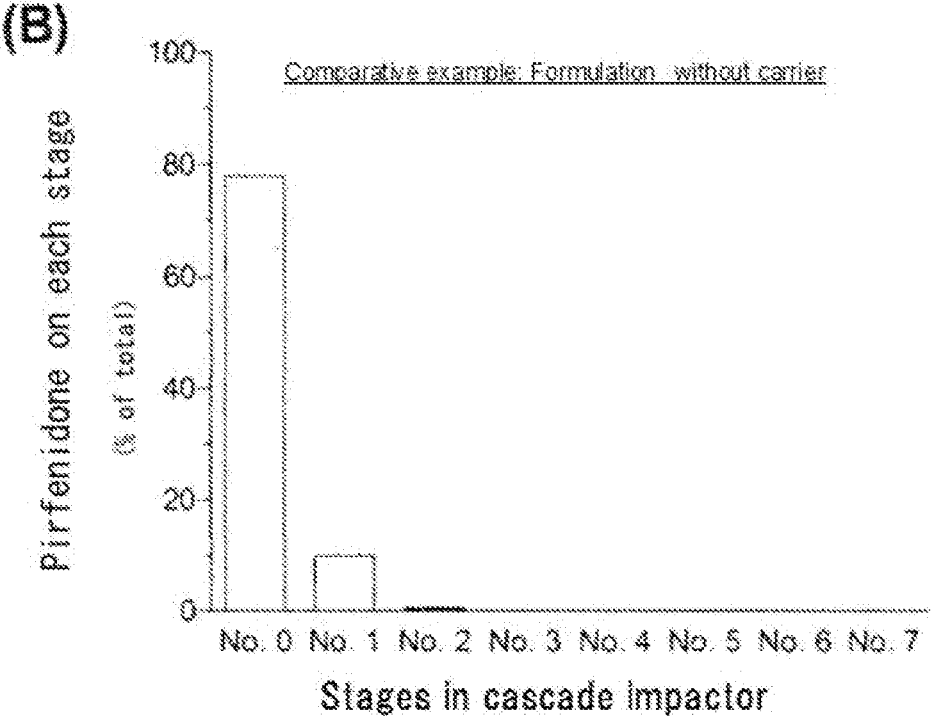

(Method)
Apparatus: Andersen sampler (AN-200, product of Shibata chemicals)
Pump flow rate: 28.3 L/min
Device used: Jet-Haler (made by UNISIA JECS)
Sample: (i) formulation 1 respirable powder formulation
(Mixing ratio; micronized particles 1 ground by jet mill: carriers=1:10)
(ii) Micronized Particles 1
(ground by jet mill, but not mixed with carriers)
A Japanese Pharmacopoeia No. 2 capsule was filled up with samples (i) and (ii) in proper quantity, respectively, and was installed in the device.
Drug determination method: (UPLC-MS analysis conditions)
Column used: Acuity UPLC BEH C 18 Column (Waters)
Detector: SQ Detector (Waters)
Pump: Binary Solvent Manager (Waters)
Flow rate of mobile phase: 0.25 mL/min
Mobile phase: A: 100% acetonitrile, B: 5 mm ammonium acetate
0~1 Min.: A 20%
1~3 Min.: A 20-95%
3~4 Min.: A 95%
Column temperature: 40° C.
(Results) The amount of pirfenidone in each stage in the body of cascade impactor is shown in FIG. 4. From assessment of aerodynamic particle size by cascade impactor, as shown in the graph of FIG. 4 (A), the respirable powder formulation (Formulation 1) of sample (i) was found to be mainly distributed in the stage 0 and the stages 2~4. The particles distributed in the stage 0 are estimated to be pirfenidone contained in the undissociated complexes of micronized particles and carriers. The dissociated micronized particles were found to be mainly distributed in the stages 2~4. The amount of percents for particles distributed in the stages 2~7 is defined by RF value specified as "a rate with which micronized particles arrive at a target site, bronchial tubes or lung." The RF value in this Example exceeds 45%. Accordingly, it is thought that the respirable formulation of the present invention, which is a complex of micronized particles and carriers, remains in respiratory tract, and only micronized particles dissociated from the complex fully reach the target site, bronchial tubes or lung.

As to the release from a capsule, high fluidity and dispersibility of the formulation were also shown, since 98.6% of the formulation was confirmed to be emitted from the capsule. On the other hand, when the sample (ii), the micronized particles 1 using no carrier, was analyzed, about 99% remained in the stages 0 and 1, and the RF value was less than 1% as shown in the graph of FIG. 4 (B). It is confirmed that sufficient dispersibility cannot be obtained without a carrier, and the fall of the inhalation properties was caused by forming agglomeration of the micronized particles.

Accordingly, in order to make the micronized particles reach the target site (bronchial tubes or lung), the powder respirable formulation using a carrier is preferred.

Example 5

(1) Preparation of a Model Animal Sensitized with Albumen Origin Ovalbumin (OVA) and Medication of the Respirable Powder Formulation (Formulation 1) in Airway Using an OVA-sensitized animal model which is a typical asthma and chronic obstructive pulmonary disease model, a medicinal effect of the respirable powder formulation of the formulation 1 was assessed. This model causes local inflammation in the respiratory organ by prescribing the OVA respirable powder formulation in airway of the animal sensitized by the OVA acting as an antigen which causes neutrophilic leukocyte inflammation and eosinophilic leukocytosis in lung. The illustrative procedure of the model preparation and the medication in airway of the respirable powder formulation of the formulation 1 are shown below.

(Procedure)
Animal: Sprague-Dawley rat (8~11 of age)
Reagents: Albumen origin ovalbumin (SIGMA) and aluminum hydroxide gel (SIGMA)
Medication instrument in airway: DP-4 (Ina Research, Inc.)
Animals were sensitized by intraperitoneal injection of the OVA solution (OVA: 0.33 mg/kg with 16.6 mg of alum) on days 0, 7, and 14. They were received intratracheal administration of the OVA respirable powder formulation (100 μg as OVA amount) at 24 h after the last OVA sensitization. The intratracheal administration was performed by sending compressed air through inserted DP-4 in the airway after anesthetized with sodium pentobarbital.

To the control group, a respirable powder formulatic a produced by using lactose was used.

Pre-medication of the formulation 1 (1 mg kg) was performed 1 hour before medication of the OVA respirable powder formulation.

TABLE 2

|  | Pre-medication | 24 hrs. after final sensitization |
| --- | --- | --- |
| OVA group | lactose-DPI | OVA-DPI |
| control goup | lactose-DPI | lactose-DPI |
| Formulation 1 group | Formulation 1 | OVA-DPI |

(2) Bronchoalveolar Lavage Fluid (BALF) Collection, and Total Cell Numbers in BALF BALF is said to be useful for diagnosis of respiratory disease. In this Example, inflammation and tissue disorders were assessed by counting the total cells in BALE. At 24 h after the OVA challenge, BALF was collected by washing the airways with 5 mL of PBS by inserting cannula into the airway after brood removal from ventral aorta under anesthesia by Nembutal. The BALF collected was pooled and centrifuged for 5 min, the supernatant was then removed, and cells were re-suspended with 1 mL of PBS. The total number of cells in BALF was counted using a manual hemocytometer under microscope.

Figure 5:
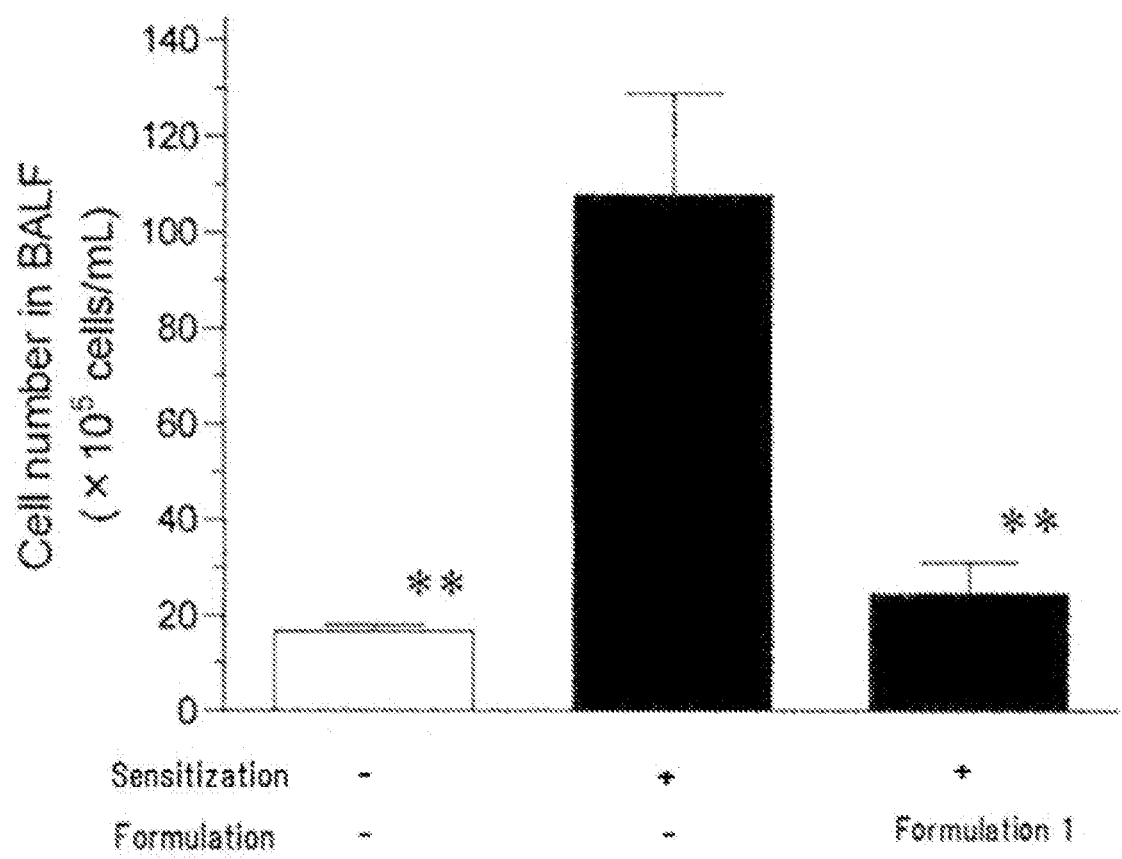
FIG. 5 shows a counting result of inflammatory cells in a broncho alveolar lavage fluid (BALF) of an asthma and chronic obstructive pulmonary disease model rat being administered with the formulation 1 by inhalation.

FIG. 5 shows the result of measurement of the inflammatory cell infiltration inhibiting activities by the formulation 1 (1 mg/kg) in an experimental asthma and chronic obstructive pulmonary disease model animal. The ordinate shows total cell numbers in BALF. The total cell numbers mainly consist of monocytes and neutrophils.

In the OVA group at 24 hours after the last sensitization, the total cell numbers increased by about 6.5-fold compared to that of the control group. On the other hand, in the formulation 1 group, the total cell numbers in BALF decreased by about 90% as compared to those of the control group.

Said inflammation decreased in a dose-dependent manner by pretreatment with the formulation 1 (0.1~3.33 mg/kg), and the total cell numbers in BALF at the time of treatment by 3.33 mg/kg was almost equivalent to the case of treatment by 1 mg/kg. These data were indicative of the therapeutic potential of the formulation 1 against inflammation in the lung local part observed in pulmonary fibrosis, asthma, etc.

(3) Measurement of Lung Inflammation Injury Biomarkers in BALF

In order to examine the pharmacologic effect of the formulation 1 in detail, various biomarkers in BALF were measured. Lactate dehydrogenase (LDH) was chosen as a biomarker of lung disorder, and myeloperoxidase (MPO) was chosen as a biomarker of neutrophilic leukocyte inflammation, respectively. In inflammation and fibrosis of the airway, MPO secreted from neutrophilic leukocyte/macrophage works as a pro-inflammatory mediator. Accordingly, the enzyme activity of MPO functions as a biomarker of neutrophilic leukocyte.

Figure 6:
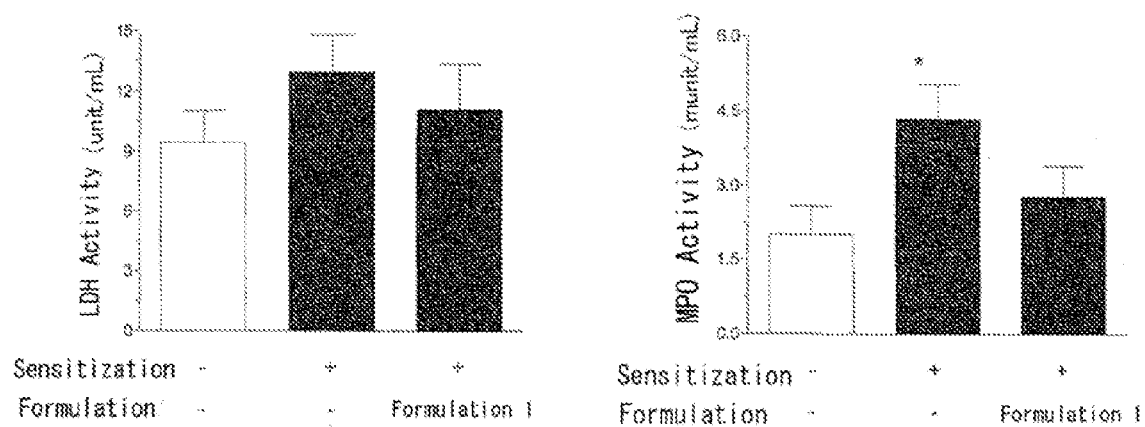
FIG. 6 shows results of biomarker measurement result of inflammatory cells in broncho alveolar lavage fluid (BALF) of the asthma and chronic obstructive pulmonary disease model rat being administered with the formulation 1 by inhalation.

Measurement results of LDH activity and MPO activity are shown in FIG. 6.

As compared to the control group, both of the LDH activity and the MPO activity in the OVA group at 24 hours after the last sensitization increased. On the other hand, in the formulation 1 group, reduction of each biomarker was observed as compared to the OVA group at 24 hours after the last sensitization. Specifically, an increase rate in which each biomarker increases from the control group by OVA sensitization was attenuated by medication of the formulation 1 to about 67% in MPO activity and to about 52% in LDH activity, respectively. Thus, the formulation 1 is thought to be efficacious for suppression of neutrophilic inflammation and imbalance of the enzyme system accompanying with it.

These observations were in agreement with the inhibitory effects on the recruitment of inflammatory cells in BALF and thus, the present data were also indicative of the topical therapeutic potential of the formulation 1 respirable powder formulation for the treatment of pulmonary inflammatory and fibrotic diseases.

Comparative Example 1

Examination of Phototoxic Reaction in Oral Administration of Pirfenidone

Hair of rats were carefully shaved by hair clipper, and pirfenidone was administered orally to the rats (160 mg/kg or 30 mg/kg), and the rats were irradiated with a black light. Colors of the skin before and after the light irradiation were evaluated with a color difference meter. The results are shown in Table 3. Change of skin color was intentionally observed in the group medicated with 160 mg/kg of pirfenidone compared to the control group, whereas significant change was not observed in the group medicated with 30 mg/kg of pirfenidone.

TABLE 3

| | UV | | L* | a* | b* | $\Delta$E |
|---|---|---|---|---|---|---|
| control | − | initial value | 64.91 | 1.26 | 7.19 | 1.13 ± 0.34 |
| | | after treatment | 65.98 | 1.03 | 7.07 | |
| | + | initial value | 71.22 | 1.30 | 2.29 | 2.26 ± 0.19 |
| | | after treatment | 69.23 | 1.92 | 3.03 | |
| pirfenidone (160 mg/kg) | − | initial value | 70.59 | 0.09 | 3.67 | 1.69 ± 0.24 |
| | | after treatment | 71.04 | −1.04 | 4.88 | |
| | + | initial value | 71.05 | 0.89 | 5.67 | 3.97 ± 0.59 |
| | | after treatment | 72.35 | 2.06 | 9.17 | |
| pirfenidone (30 mg/kg) | − | initial value | 70.16 | 1.19 | −0.18 | 1.47 ± 0.27 |
| | | after treatment | 71.56 | 1.54 | −0.36 | |
| | + | initial value | 72.90 | 1.27 | 4.14 | 2.40 ± 0.20 |
| | | after treatment | 72.26 | 2.81 | 5.72 | |

Column header: evaluation of color change

Example 6

Pharmacokinetics (1) of Pirfenidone at the Time of Airway Administration of the Formulation 1

The respirable powder formulation of pirfenidone resulted in marked decrease in the amount of necessary dose as compared to the oral administration. However, the possibility of risk reduction of photodermatosis is not clear. In general, since drug-induced photodermatosis appear in the skin and eyes, the specific distribution of drug molecules in the skin and/or eyes could be a key consideration for evaluating the photodermatosis risk. Then, in order to verify the photosafety of the formulation 1, a pharmacokinetic study was undertaken after intratracheal administration of the formulation 1 at a pharmacologically effective dose (1 mg/kg). Additionally, since in the oral administration, both pharmaceutically effective and phototoxic dose (160 mg/kg) and pharmaceutically non-effective and non-phototoxic dose (30 mg/kg) are known, pharmacokinetic parameters were obtained after oral administration at both doses. Concentration-time curves of pirfenidone in the plasma, skin, lung, and eyes were obtained by UPLC/ESI-MS analysis after intratracheal and oral administrations. Relevant pharmacokinetic parameters of pirfenidone, including $C_{max}$, $t_{1/2}$, $AUC_{0 \to \infty}$, and MRT, were summarized in Table 4. After oral administration of pirfenidone, plasma and lung concentrations of pirfenidone immediately reached the $C_{max}$ within 5 min and these concentrations decreased steadily with half lives of ca. 0.3-0.8 h. With respect to skin and eye depositions, reaching maximum levels at ca. 0.5 h after oral dosing, followed by an elimination phase with a half-life of ca. 0.7-1.1 h. Thus, the elimination of pirfenidone from the skin and eyes was found to be slower than that in plasma and pirfenidone may accumulate in these light-exposed areas (skin and eyes) upon chronic dosing, resulting in an increased photodermatosis risk. In contrast, after intratracheal administration of the formulation 1, each of plasma and tissue concentrations of pirfenidone immediately reached the $C_{max}$ within 5 min, and then, these medicaments rapidly diminished below detectable levels within 1.5 h.

The intra airway administration of the formulation 1 (1 mg/kg) led to ca. 440-, 90-, and 30-fold reductions in $C_{max}$ values for plasma, skin, and eyes, respectively, compared to the orally-taken pirfenidone at the photodermatosis expression dose (160 mg/kg). The AUC values in plasma, skin, and eyes decreased by ca. 1,800-, 370-, and 440-fold, respectively. From these studies, it was confirmed that the intratracheal administration of pirfenidone successfully resulted in marked decrease in systemic exposure, compared to the oral administration.

In addition, there were still ca. 63~70-fold differences in AUC values for skin and ocular pirfenidone between the oral formulation (30 mg/kg) and the respirable formulation (1 mg/kg) at non-photodermatosis level of doses. The differences of these pharmacodynamics coefficients show that use by inhalation of pirfenidone decreases notably the accumulation in skin and eyes and the systemic exposure of pirfenidone compared to the oral administration. Even if compared with dose which does not reveal photodermatosis by taking orally, blood level after inhalation of the formulation 1 shows notably low value. This suggests that it becomes possible for application of this pharmaceutical technology to raise effect in lung local part of this agent, and to reduce remarkably the risk of onset of the side effect, photodermatosis, further.

TABLE 4

PK parameters of plasma and tissues on PFD in rats after oral intratracheal administrations

| Samples | $C_{max}$ (plasma, µg/mL; tissues, µg/g tissue) | $t_{1/2}$ (h) | $AUC_{0 \to \infty}$ (plasma, h · µg/mL; tissues, h · µg/g tissue) | MRT (h) |
|---|---|---|---|---|
| Plasma | | | | |
| PFD-RP (1 mg/kg, i.t.) | 0.307 ± 0.039 | 0.17 ± 0.02 | 0.0835 ± 0.011 | 0.261 ± 0.011 |
| PFD (30 mg/kg, p.o.) | 19.7 ± 0.93 | 0.33 ± 0.02 | 14.1 ± 0.92 | 0.667 ± 0.094 |
| PFD (160 mg/kg, p.o.) | 135 ± 11 | 0.53 ± 0.03 | 152 ± 10 | 1.05 ± 0.075 |
| Skin | | | | |
| PFD-RP (1 mg/kg, i.t.) | 0.369 ± 0.014 | 0.24 ± 0.02 | 0.183 ± 0.029 | 0.427 ± 0.0051 |
| PFD (30 mg/kg, p.o.) | 8.16 ± 0.47 | 1.07 ± 0.28 | 11.5 ± 0.51 | 1.14 ± 0.12 |
| PFD (160 mg/kg, p.o.) | 32.9 ± 2.6 | 1.06 ± 0.24 | 68.0 ± 1.4 | 1.70 ± 0.043 |
| Lung | | | | |
| PFD-RP (1 mg/kg, i.t.) | 0.271 ± 0.035 | 0.276 ± 0.077 | 0.136 ± 0.039 | 0.421 ± 0.0080 |
| PFD (30 mg/kg, p.o.) | 6.46 ± 0.69 | 0.799 ± 0.24 | 6.45 ± 0.43 | 0.787 ± 0.16 |
| PFD (160 mg/kg, p.o.) | 37.6 ± 5.7 | 0.766 ± 0.16 | 52.1 ± 1.0 | 1.32 ± 0.041 |

TABLE 4-continued

PK parameters of plasma and tissues on PFD in rats after oral intratracheal administrations

| Samples | $C_{max}$ (plasma, μg/mL; tissues, μg/g tissue) | $t_{1/2}$ (h) | $AUC_{0\to\infty}$ (plasma, h · μg/mL; tissues, h · μg/g tissue) | MRT (h) |
|---|---|---|---|---|
| Eyes | | | | |
| PFD-RP (1 mg/kg, i.t.) | 0.202 ± 0.19 | 0.266 ± 0.059 | 0.120 ± 0.030 | 0.554 ± 0.0084 |
| PFD (30 mg/kg, p.o.) | 3.95 ± 0.30 | 0.668 ± 0.18 | 8.33 ± 0.39 | 1.06 ± 0.13 |
| PFD (160 mg/kg, p.o.) | 26.0 ± 2.6 | 1.06 ± 0.27 | 58.8 ± 1.3 | 1.93 ± 0.051 |

Each parameter was calculated on the basis of concentration-time curves in plasma and tissues. i.t.: intratracheal administration; and p.o.: oral administration.
Each value represents mean ± S.E. for 4-8 rats.
PFD-RP: Pirfenidone Respirable Powder
PFD: Pirfenidone Example 7

Pharmacokinetics 2 of Pirfenidone at the Time of Air a Administration of the Formulation 1

Figure 7:
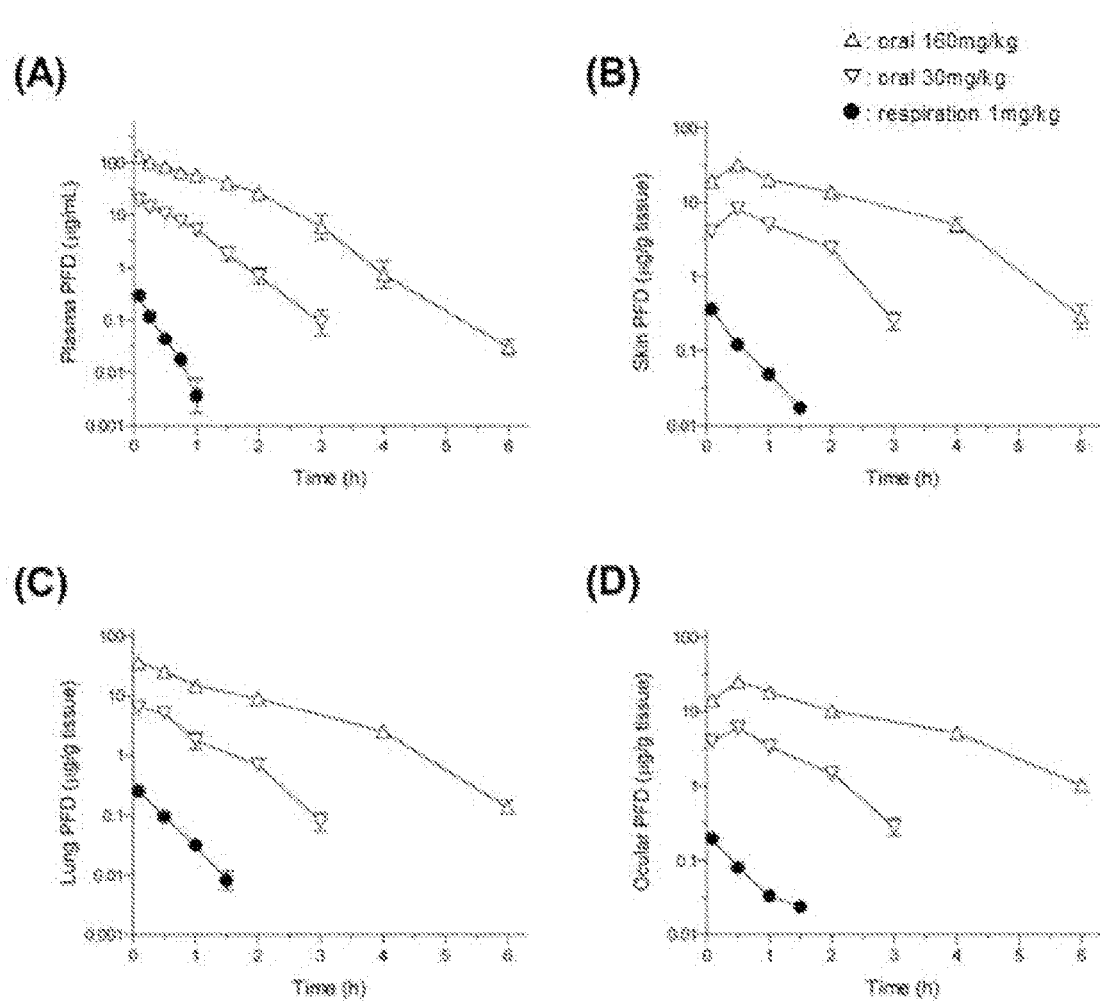
FIG. 7 shows the amount of transmigration of pirfenidone to each tissue at the time of carrying out single-dose administration of the oral and respirable formulations. Symbols represent; △: oral pirfenidone 160 mg/kg, ▽: oral pirfenidone 30 mg/kg, and ●: 1 mg/kg of the respirable powder formulation of pirfenidone.

Similarly to Example 5, single-dose administrations of pirfenidone orally and the formulation 1 by inhalation were performed in rats, and the amount of transmigration of pirfenidone to each tissue was monitored by UPLC/ESI-MS. Results are shown in FIG. 7. When compared in dose (160 mg/kg) having an anti-inflammatory activity, while the amount of skin-transmigration of pirfenidone in 1 hour after administration was about 50 ng/g-tissue via inhalation (1 mg/kg), the amount via oral administration (160 mg/kg) was about 20 μg/g-tissue. From this, while the amount of medication in inhalation is 1/160 in the case of oral administration, the amount of skin transmigration in inhalation decreases to 1/400 of oral formulation. Significant reduction of the amount of skin transmigration of pirfenidone like this suggests large mitigation of side effects by the present invention. Thus, the respirable formulation of the present invention has an excellent effect.

Pirfenidone Pharmacokinetics (3) at the Time of Airway Administration of the Formulation 1

Figure 8:
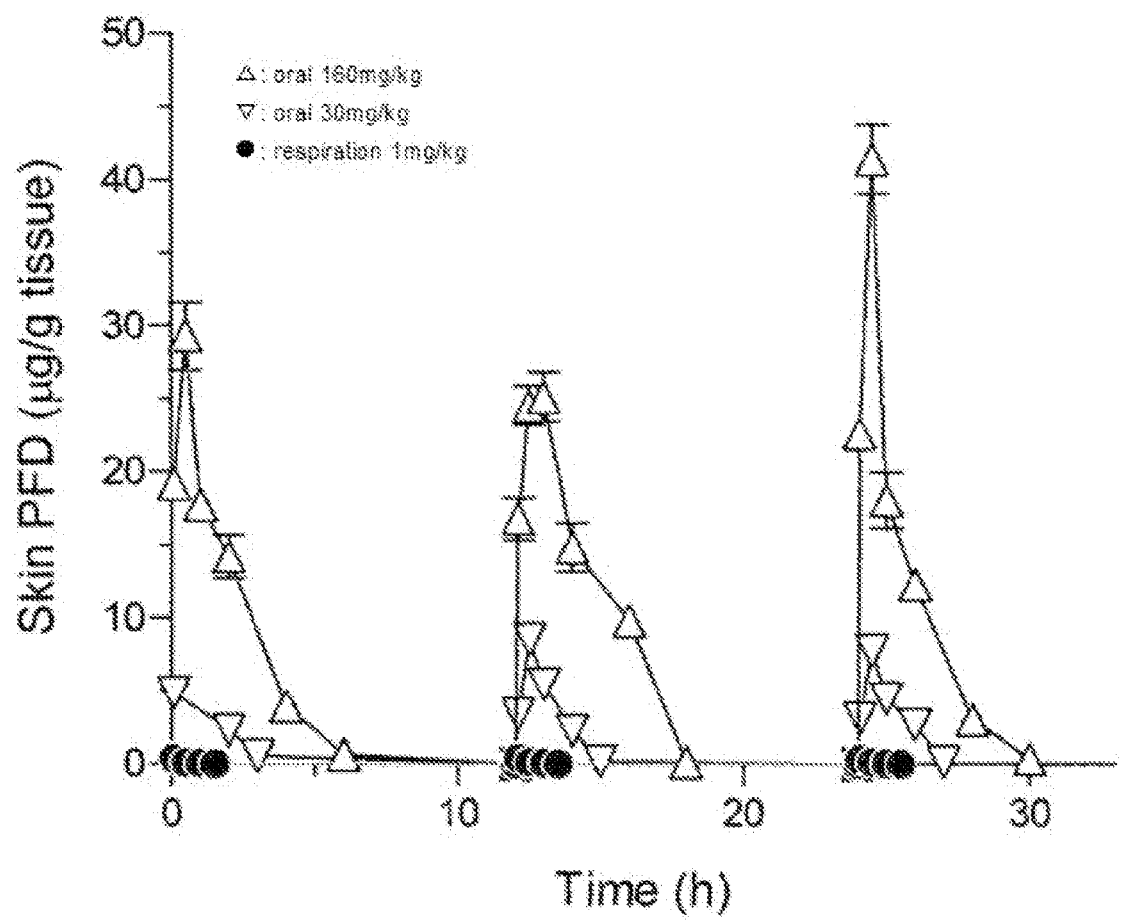
FIG. 8 shows a concentration change of pirfenidone in skin at the time of administering oral and respirable formulations repeatedly. Symbols represent; △:oral pirfenidone 160 mg/kg, ▽: oral pirfenidone 30 mg/kg, and ●: 1 mg/kg of the respirable powder formulation of pirfenidone.

Results of having monitored the amount of skin transmigration of pirfenidone in repeated-dose administrations by oral and inhalation are shown in FIG. 8. Although a temporary elevation of the pirfenidone concentration in the skin was observed by pirfenidone oral administration (30, 160 mg/kg) also in repeated-dose administrations in every 12 hours, the elevation disappeared in about 6 hours after administration. In repeated-dose administrations, pirfenidone did not show any accumulation trend. At the time of inhalation of the formulation 1, lower skin transitionality was observed more remarkably than the time of administration of oral dose (30 mg/kg) which does not show photodermatosis, and similarly, no accumulation trend was shown. From this, the systemic side effect is considered to be avoidable even when the respirable formulation is used repeatedly.

INDUSTRIAL APPLICABILITY

The present invention provides the powder formulation which reduces side effect risk of medicine having a side effect of a drug-induced photodermatosis and increases therapeutic effect, and the method for producing the same. Since the powder formulation of the present invention makes inhalation therapy possible by the ability of easy aerosolizability and thus increases pharmacological effect in lung local part, the reduction of dose becomes possible. The skin transmigration of the aforementioned medicine can be controlled with a lung specific delivery technology, and thus, photodermatosis, a side effect, can be controlled.

The invention claimed is:

1. A powder formulation comprising:
   (i) micronized particles with a mean particle diameter of 20 μm or less comprising
      (i-1) pirfenidone and
      (i-2) at least one excipient selected from the group consisting of a saccharide, a sugar alcohol, a fatty acid and salts thereof, a wax, calcium sulfate, calcium carbonate, talc and titanium oxide,
      wherein the micronized particles exclude a polymer, and
   (ii) a carrier with a mean particle diameter of 10 to 200 μm, wherein the micronized particles are adhered to the carrier.

2. The powder formulation according to claim 1, wherein a particle diameter of the micronized particles is smaller than a mean particle diameter of the carrier.

3. The powder formulation according to claim 1, wherein the saccharide is lactose.

4. The powder formulation according to claim 1, wherein the sugar alcohol is erythritol.

5. The powder formulation according to claim 1, wherein the excipient is erythritol and the carrier is lactose.

6. The powder formulation according to claim 1, wherein a weight ratio between the pirfenidone and the excipient is in the range of 1:5000 to 10:1.

7. The powder formulation according to claim 1, wherein a weight ratio between the micronized particles and the carrier is in the range of 1:100 to 10:1.

8. The powder formulation according to claim 1, wherein a mean diameter of the micronized particles is in the range of 1 to 9 μm.

9. The powder formulation according to claim 1, wherein the powder formulation is a transpulmonary inhalation formulation.

10. The powder formulation according to claim 1, wherein a drug-inducement of photodermatosis of the pirfenidone has been reduced as compared with an oral administration formulation.

11. A process for producing the formulation according to claim 1, comprising:
    mixing micronized particles with a mean particle diameter of 20 μm or less comprising pirfenidone and an excipient with a carrier having a particle diameter of 10 to 200 μm.

12. The process according to claim 11, wherein the micronized particles are prepared by mixing the pirfenidone and the excipient to obtain a mixture, and then micronizing the mixture with a jet mill.

13. The process according to claim 12, wherein the micronized particles and the carrier are mixed in a container made from nylon or polyethylene.

14. The process according to claim 11, wherein the micronized particles and the carrier form a complex.

15. An inhalation formulation obtained by the process according to claim 11.

* * * * *